United States Patent [19]

Moeller et al.

[11] Patent Number: 4,684,665
[45] Date of Patent: Aug. 4, 1987

[54] SEBOSUPPRESSIVE BENZOIC ACID ESTER DERIVATIVES AND COSMETIC PREPARATIONS CONTAINING THEM

[75] Inventors: Hinrich Moeller; Siegfried Wallat, both of Monheim, Fed. Rep. of Germany

[73] Assignee: Henkel Kommanditgesellschaft auf Aktien, Dusseldorf, Fed. Rep. of Germany

[21] Appl. No.: 818,648

[22] Filed: Jan. 10, 1986

[30] Foreign Application Priority Data

Jan. 14, 1985 [DE] Fed. Rep. of Germany ....... 3500971

[51] Int. Cl.$^4$ ............................................ C07C 69/76
[52] U.S. Cl. .................................... 514/543; 514/533; 560/64
[58] Field of Search ................... 560/64; 514/543, 533

[56] References Cited

FOREIGN PATENT DOCUMENTS 2021227 11/1970 Fed. Rep. of Germany .
2439458 2/1975 Fed. Rep. of Germany .

OTHER PUBLICATIONS

Baggaley, K. et al., J. Med. Chem. 20(11), 1388-93, 1977.

*Primary Examiner*—Paul J. Killos
*Attorney, Agent, or Firm*—Ernest G. Szoke; Henry E. Millson, Jr.; Mark A. Greenfield

[57] ABSTRACT

A cosmetic preparation for the treatment of seborrhea containing an antiseborrheically effective amount of a p-alkoxy or p-alkylbenzyloxy benzoic acid ester having the formula

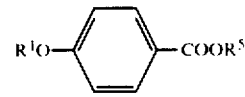

wherein $R^1$ is
(i) a branched alkyl group having from 6 to 18 carbon atoms,
(ii) an alkylbenzyl group wherein the alkyl moiety has from 3 to 9 carbon atoms, or
(iii) $R^2$—(O—Y)$_n$ wherein $R^2$ is an alkyl group havig from 6 to 18 carbon atoms, or an alkylbenzyl group wherein the alkyl moiety has from 3 to 9 carbon atoms; Y is CHR$^3$—CHR$^4$; $R^3$ and $R^4$ independently represent a hydrogen or a methyl, and n=1 or 2;

and $R^5$ is an alkyl group having from 1 to 4 carbon atoms, or a methoxy alkyl, an ethoxyalkyl, or a hydroxyalkyl having from 1 to 4 carbon atoms; and further containing conventional vehicles and additives; the process for reducing mammalian sebum production by using the above cosmetic preparation and the p-alkoxy and p-alkylbenzyloxy benzoic acid esters themselves.

21 Claims, No Drawings

SEBOSUPPRESSIVE BENZOIC ACID ESTER DERIVATIVES AND COSMETIC PREPARATIONS CONTAINING THEM

BACKGROUND OF THE INVENTION

1. Field of the Invention

This invention relates to topical cosmetic preparations for improving the oily and unaesthetic appearance of hair and skin. This invention particularly relates to certain benzoic acid ester derivatives and to cosmetic preparations containing them.

2. Description of Related Art

In modern cosmetology, researchers continue to look for cosmetic preparations which will reduce the oily and unaesthetic appearance of the hair and scalp caused by excessive secretion of the sebaceous glands. By treating hair and scalp with suitable cosmetic preparations, secretion of the sebaceous glands may be reduced to a normal level and oily hair may be restored to a healthy appearance.

In the past, cosmetic preparations such as shampoos containing sulfur, mercury or tar additives have been used to control seborrhea of the scalp. Unfortunately, prolonged use of these known antiseborrheic additives frequently caused unwanted side effects, without giving really satisfactory results with regard to efficacy and performance properties. Certain derivatives of benzoic acid esters also have been described as antiseborrheic additives for cosmetic preparations (see U.S. Pat. Nos. 4,503,244 and 4,545,984). Nonetheless, a need still exists for topical cosmetic preparations showing enhanced sebosuppressive activity.

An object of the present invention is to provide a cosmetic preparation which exhibits an improved antiseborrheic activity as compared with known preparations but does not contribute to any adverse consequences on the human body.

DESCRIPTION OF THE INVENTION

It has now been found, quite unexpectedly, that certain benzoic acid ester derivatives, referred to hereafter as alkoxy or alkylbenzyloxy benzoic acid esters, possess outstanding antiseborrheic activity, even in very small doses. Surprisingly, the antiseborrheic effect obtained using these materials is considerably better than that obtained using known benzoic acid esters. Consequently, these new alkoxy and alkylbenzyloxy benzoic acid esters can be used in smaller quantities in sebosuppressive cosmetic preparations.

Accordingly, the present invention relates to a sebosuppressive cosmetic preparation containing an antiseborrheically effective amount of a p-alkoxy or p-alkylbenzyloxy benzoic acid ester corresponding to the following formula

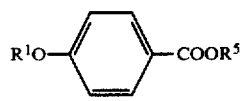
(I)

wherein $R^1$ is (i) a branched alkyl group having from 6 to 18 carbon atoms, (ii) an alkylbenzyl group wherein the alkyl moiety has from 3 to 90 carbon atoms, or (iii) $R^2-(O-Y)_n-$ wherein $R^2$ is an alkyl group having from 6 to 18 carbon atoms, or an alkylbenzyl group wherein the alkyl moiety has from 3 to 9 carbon atoms; Y is $CHR^3-CHR^4$; $R^3$ and $R^4$ independently represent a hydrogen or a methyl, and n=1 or 2;

and $R^5$ is an alkyl group having from 1 to 4 carbon atoms, or a methoxy alkyl, an ethoxyalkyl, over a hydroxyalkyl having from 1 to 4 carbon atoms. Generally, the sebosuppressive cosmetic preparation further includes conventional vehicles and additives for facilitating topical application.

The present invention also relates to a process for reducing the production of sebum by the sebaceous cell in mammals which comprises contacting said sebaceous cell with an antiseborrheically effective amount of the compound of formula I, as defined above.

The present invention further relates to a p-alkoxy or p-alkylbenzyloxy benzoic acid ester having the formula

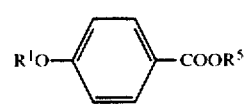
(I)

wherein $R^1$ is (i) a branched alkyl group having from 6 to 18 carbon atoms, (ii) an alkylbenzyl group wherein the alkyl moiety has from 3 to 9 carbon atoms, or (iii) $R^2-(O-Y)_n$ wherein $R^2$ is an alkyl group having from 6 to 18 carbon atoms, or an alkylbenzyl group wherein the alkyl moiety has from 3 to 9 carbon atoms; Y is $CHR^3-CHR^4$; $R^3$ and $R^4$ independently represent a hydrogen or a methyl, and n=1 or 2;

and $R^5$ is an alkyl group having from 1 to 4 carbon atoms, or a methoxy alkyl, an ethoxyalkyl, or a hydroxyalkyl having from 1 to 4 carbon atoms.

The compounds used in accordance with the present invention are new. They may be produced by generally known methods.

For example, the esters of the present invention may be prepared by alkylation or aralkylation of the corresponding 4-hydroxybenzoic acid esters with halides or ether halides containing radicals corresponding to $R^1$ as defined above. These esters also may be prepared by esterification of para-substituted benzoic acid (substituted by radicals corresponding to $R^1O$) with hydroxyalkyl compounds corresponding to $R^5$ such as alcohols and hydroxy-terminated ethers. Specific esters may also be obtained by transesterification. For example p-alkoxy or p-alkylbenzyloxy benzoic acid methyl esters may be transesterified in the presence of alkaline catalysts such as sodium methylate with suitable alcohol components containing radicals corresponding to $R^5$ as described above. Methanol liberated during the reaction is removed from the equilibrum reaction mixture by distillation.

For example, compounds of this invention may be produced by esterification of the following benzoic acid derivatives using hydroxyalkyl compounds corresponding to $R^5$:

(I) those wherein $R^1$ is a branched alkyl group having from 6 to 18 carbon atoms or an alkylbenzyl group wherein the alkyl moiety has from 3 to 9 carbon atoms and the alkyl moiety preferably is branched such as 4-(3,3-dimethyl-1-butoxy)-benzoic acid,
4-(3,3-dimethyl-2-butoxy)-benzoic acid,
4-(2-methyl-1-, -2- or -3-pentoxy)-benzoic acid,
4-(3- or 4-methyl-1-pentoxy)-benzoic acid,
4-(3-ethyl-3-pentoxy)-benzoic acid,
4-(2- or 3-hexoxy)-benzoic acid,
4-(2-heptoxy)-benzoic acid,
4-(4-heptoxy)-benzoic acid,
4-(2,4,4-trimethyl-1-pentoxy)-benzoic acid,
4-(2-, 3- or 4-octyloxy)-benzoic acid,
4-(2-ethylhexyloxy)-benzoic acid,
4-(3,5,5-trimethyl-1-hexyloxy)-benzoic acid,
4-(3- or 5-nonyloxy)-benzoic acid,
4-(3,7-dimethyl-1-octyloxy)-benzoic acid,
4-(5-undecyloxy)-benzoic acid,
4-(2,4,6-trimethyl-1-nonyloxy)-benzoic acid,
4-(2-butyl-1-octyloxy)-benzoic acid,
4-isotridecyloxy-benzoic acid,
4-(2-hexyl-1-decyloxy)-benzoic acid,
4-isooctadecyloxy-benzoic acid,
4-[2-(4,4-dimethyl-2-pentyl)-5,7,7-trimethyl-1-octyloxy]-benzoic acid,
4-(3- or 4-isopropyl-benzyloxy)-benzoic acid,
4-(2-, 3- or 4-tert-butylbenzyloxy)-benzoic acid,
4-[4-(3,3-dimethyl-1-butyl)-benzyloxy]-benzoic acid,
4-[4-(2,4,4-trimethyl-1-pentyl)-benzyloxy]-benzoic acid,
4-[4-(2-ethylhexyl)-benzyloxy]-benzoic acid, and
4-[4-(3,5,5-trimethyl-hexyl)-benzyloxy]-benzoic acid.

Preferred compounds are those in which $R^1$ is a branched chain alkyl group having from 8 to 13 carbon atoms and in particular is a repeatedly branched $C_8$–$C_{13}$ alkyl or is an alkylbenzyl group wherein the alkyl moiety has from 3 to 6 carbon atoms, and the alkyl moiety preferably is branched and (II) those wherein $R^1$ is $R^2$—(O—Y)$_n$ where $R^2$ and Y are as defined above such as 4-(2-octyloxy-ethoxy)-benzoic acid,
4-(1-nonyloxy-2-propoxy)-benzoic acid,
4-(2-decyloxy-1-propoxy)-benzoic acid,
4-(2-undecyloxy-ethoxy)-benzoic acid,
4-(2-dodecyloxy-ethoxy)-benzoic acid,
4-[2-(2-dodecyloxy-ethoxy)-ethoxy]-benzoic acid,
4-(1-dodecyloxy-2-propoxy)-benzoic acid,
4-[1-(1-tetradecyloxy-2-propoxy)-2-propoxy]-benzoic acid,
4-(2-hexadecyloxy-ethoxy)-benzoic acid, and
4-[2-(2-hexadecyloxy-ethoxy)-ethoxy]-benzoic acid.

Preferred compounds of group (II) are those in which $R^2$ is an alkyl group having from 9 to 14 carbon atoms and n=1.

As noted above, the compounds of groups (I) and (II) are esterified with hydroxyalkyl compounds corresponding to $R^5$. Examples of suitable $R^5$ radicals are methyl, ethyl, propyl, isopropyl, butyl, 2-butyl, 2-hydroxy-ethyl or -propyl, 2-methoxy-ethyl or -propyl, 2-ethoxy-ethyl, 3-hydroxy-propyl or -butyl.

The compounds of the present invention show pronounced sebosuppressive activity combined with excellent compatibility with the skin and mucous membrane. They may be incorporated without difficultly in various cosmetic preparations, such as aqueous or alcoholic solutions, oils, suspensions, gels, emulsions, salves or aerosols. The greater solubility in water and resistance to hydrolysis of these p-alkoxy and p-alkylbenzyloxy benzoic acid esters as compared with the prior art esters are particularly advantageous for the preparation of such products. For treating seborrheic skin and oily hair, these preparations may be applied in any of the usual forms, such as hair lotions, shampoos, hair treatments, hair rinses, skin lotions or shaking mixtures containing any of the conventional vehicles and additives for facilitating topical application. A shampoo is a particularly effective form for treating very oily hair.

The cosmetic preparations according to the invention represent solutions and dispersions of an effective amount of the compounds of formula I in water, in alcohol—especially ethanol, in aqueous-alcoholic mixtures, in oil, as well as in suspensions, gels, emulsions, salves, pastes, or aerosols. Preferably these alkoxy and alkylbenzyloxy benzoic acid esters are used as an ingredient in known hair care preparations. In addition to including an active substance according to the invention, these cosmetic preparations may contain standard auxiliaries and vehicles, such as water, organic solvents, surfactants, oils, fats, waxes, fragrances, dyes, preservatives and the like.

Preferably, the sebosuppressive preparation contains from about 0.005 to 5% by weight and more preferably from about 0.01 to 2% by weight of the benzoic acid ester derivatives of the present invention. As will be demonstrated in the Examples which follow, due to the improved antiseborrheic activity of the benzoic acid ester derivatives of this invention, sebosuppressive cosmetic preparations can be formulated having a much lower amount of the active substance than was possible using prior art materials.

While preparations according to the invention can be used daily, satisfactory results also can be obtained using a single weekly application. By employing the cosmetic preparations of this invention, the oily appearance of hair is reduced, and fat production delayed, so that normal hair care is possible. The individual dose to be used in each treatment is not critical and harmful side effects have not been observed.

The following examples are presented to illustrate further the present invention and are not intended to limit its scope which is defined by the appended claims.

PRODUCTION EXAMPLES (A) 4-2(2-ethylhexyloxy)-benzoic acid methylester

A mixture of 51.7 g (0.34 mol) of 4-hydroxybenzoic acid methylester, 500 ml of dimethyl formamide, 60 g (0.40 mol) of 2-ethylhexylchloride and 21.8 g (0.40 mol) of sodium methylate was heated for 7 hours to boiling temperature and, after cooling and removal of the sodium chloride by filtration, was evaporated to dryness under reduced pressure. The residue was dissolved in methylene chloride and chromatographed (eluent: methylene chloride) on silica gel (Merck) to yield 43 g (48% of the theoretical) of 4-(2-ethylhexyloxy)benzoic acid methylester. A refractive index of $n_D^{20} = 1.5050$ was obtained from TLC-pure fractions of the recovered product.

The following compounds were obtained using a similar procedure:

(B) 4-(isononyloxy)-benzoic acid methylester
(=4-(3,5,5-trimethylhexyloxy)-benzoic acid methylester)

The product recovered exhibited a refractive index of
$n_D^{20} = 1.5030$
and a boiling point of 142°–144° C./0.013 mbar.

(C) 4-(2-hexyl-decyloxy)-benzoic acid methyester

The product recovered exhibited a refractive index of $n_D^{20} = 1.5050$ (D) 4-isooctadecyloxy benzoic acid methylester
(=4-[2-(4,4-dimethyl-2-pentyl)-5,7,7-trimethyl-1-octyloxy]-benzoic acid methylester)

The product recovered exhibited a refractive index of $n_D^{20} = 1.4927$ (E) 4-(4-tert-butylbenzyloxy)-benzoic acid methylester The product recovered exhibited a melting point of 62°-64° C.

(F) 4-(2-dodecyloxy-ethyoxy)-benzoic acid methylester

A mixture of 20.4 g (0.134 mol) of 4-hydroxybenzoic acid methylester, 200 ml of dimethyl formamide, 40 g (0.160 mol) of 2-dodecyloxy ethylchloride (from 2-dodecyloxy ethanol and thionyl chloride) and 8.6 g (0.160 mol) of sodium methylate was heated for 7 hours to boiling temperature and, after cooling and removal of the sodium chloride by filtration, was evaporated to dryness. The residue was dissolved in methylene chloride and subjected to column chromatography (silica gel, Merck using methylene chloride as the eluent). After recrystallization from methanol, the combined fractions after TLC gave 30 g (61% of the theoretical) of pure 4-(2-dodecyloxyethoxy)-benzoic acid methylester melting at 40° to 42° C.

(G) 4-[2-(2-dodecyloxy-ethoxy)-ethoxy]-benzoic acid methylester

This compound was produced in the same way as compound (A). The product recovered exhibited a refractive index of
$n_D^{20} = 1.4740$ (H) 4-(2-dodecyloxy-ethoxy)-benzoic acid-3-hydroxypropyl ester A mixture of 12 g (0.03 mol) of 4-(2-dodecyloxy-ethoyoxy)-benzoic acid methylester, 60 ml of 1,3-propanediol and 0.2 g of sodium methylate was heated for 6 hours to 150° C., methanol distilling off. After cooling, the reaction product was dissolved in methylene chloride, washed with water, dried with sodium sulfate and concentrated by evaporation. 4-(2-dodecyloxy-ethoxy)-benzoic acid-3-hydroxyproyl ester melting at 38° to 40° C. was obtained in a yield of 13 g (95% of the theoretical). After recrystallization from petroleum ether, the melting point rose to 40°-42° C.

(I) 4-isotridecyloxy-benzoic acid methylester

This compound was prepared from 4-hydroxybenzoic acid methylester and isotridecylchloride, initially obtained from isotridecanol (an oxalcohol prepared from tetrapropylene) using known techniques. The product recovered exhibited a refractive index of
$n_D^{20} = 1.5011$
and a boiling point of 197°-200° C./0.74 mbar.

TESTING FOR ANTI-SEBORRHEIC ACTIVITY

The anti-seborrheic effect obtained with compounds (B), (E), (F), (H) and (I) prepared above was closely examined using the following animal tests. Male Wistar rats having a body weight ranging from 220 to 230 g at the beginning of the tests were used as the test animals. The accumulation of sebum in the test animals was examined by visually observing the degree of browning on the shaved back of the rats. Browning is caused by the accumulation of the brown skin surface lipid secreted by the rats. This test is based on the observation that young female rats, as well as male rats washed with a surfactant solution or with a lipid solvent or male rats systematically treated with estrogens show only a normal light, pink-colored skin after shaving, while at the same time, only comparatively very small quantities of lipids can be extracted from the shaved hairs.

In order to assess the anti-seborrheic effectiveness of the alkoxy and alkylbenzyloxy benzoic acid esters of the present invention, alcoholic solutions of test substances (B), (E), (F), (H) and (I) were each brushed onto one side of the back of 6 rats. The benzoic acid ester derivatives tested were applied in concentrations ranging from 0.02 to 0.1 wt. % in the alcohol. The other side of the back of each rat was treated only with solvent without an active substance (control side).

The test period consisted of 14 days. The test substances were applied, once daily on 9 of the 14 days. A second group of 6 rats which were not treated was used as an additional control. At the end of the test period, the backs and sides of the animals were shaved and visually inspected. The examination was done independently by an evaluation panel composed of 6 people using double blind techniques.

EVALUATION METHODS

The rats can be rated on the basis of two criteria. A first criterion is the difference in coloration between the righthand side and the lefthand side of the treated rats. Each examiner awards 1 point per animal on the following basis:

| | |
|---|---|
| darker side | 1 point |
| lighter side | 0 point and |
| both sides the same | 0.5 point |

A significant difference between an untreated and treated side in this method of evaluation indicates the local effectiveness of a substance.

A second criterion of evaluation is the intensity of the brown coloration in the shaved area. The following scale is used for this analysis:

3 points dark brown
· 2 points medium brown
1 point light brown
0 points no browning According to this second method of evaluation, differences in the total points between the untreated control animals and the treated and untreated sides (ΔP) of the test animals respectively are calculated. Significant differences between the total point values assigned to the control animals and the values assigned to the treated side of the test animals again indicate the antiseborrheic effectiveness of a substance.

At the same time, there also generally is a distinct difference between the values assigned to the untreated and treated sides of the test animals. However, due to various reasons, including for example mechanical transfer of substance from one side of the animal to the other or solvent influence, this difference is not always as distinct as that observed between the control animals and the treated side of the test animals.

The following analysis scheme can be used to differentiate and quantify the effects observed according to evaluation methods 1 and 2:

| Symbol | Point difference |
| --- | --- |
| + + | very large ($\geq 99.9\%$ probability) |
| + | significant ($\geq 95\%$ probability) |
| − | ($< 95\%$ probability) |

PERCENT SEBUM REDUCTION

Results obtained with the animals tested as outlined above using the second evaluation method are set forth in the following Table. The results are presented in terms of sebum reduction percentage. The sebum reduction percentage is calculated from the point differences by determining the quotient of the difference in total points between the control group and the treated side of the test animals ($\Delta P$) and the total number of points for the control group ($P_k$) and then expressing the value obtained in percent.

$$\text{Percent Sebum reduction} = \frac{\Delta P}{P_k} \cdot 100 \, [\%]$$

TABLE
Evaluation of the sebosuppressive effects

| Compound Tested | % Sebum reduction at the indicated concentration of active substance | | |
| --- | --- | --- | --- |
| | 0.1% | 0.05% | 0.02% |
| B | 76 | 36 | — |
| E | — | 77 | 10 |
| F | — | 63 | — |
| H | — | 71 | — |
| I | — | 83 | 83 |
| 4-dodecyloxy benzoic acid methyl ester (U.S. Pat. No. 4,545,984) | 18 | 0 | — |
| 4-dodecyloxy benzoic acid-3-hydroxypropyl ester (U.S. Pat. No. 4,503,244) | 33 | 18 | — |

The superior effect of the compounds of the present invention relative to the benzoic acid esters of the prior art is clear from the values shown in the Table.

EXAMPLES OF FORMULATIONS

Specific formulations for topical cosmetic preparations of the present invention useful for the treatment of very oily hair and seborrheic skin are presented below:

| | Percent by weight |
| --- | --- |
| 1. Hair Lotion | |
| Ethanol (96%) or isopropanol | 54.0% |
| Compound B or H | 0.2% |
| Perfume oil | 0.5% |
| Water | 45.3% |
| 2. Shampoo for oily hair | |
| Ammonium lauryl sulfate containing 33 to 35% of washing-active substance | 42.0 |
| Coconut oil fatty acid diethanolamide | 3.0 |
| Sodium chloride | 2.0 |
| Sodium sulfate | 2.0 |
| Compound E or F | 1.5 |
| Preservative | 0.1 |
| Perfume oil | 0.1 |
| Water | 49.3 |
| 3. Hair treatment | |
| Glycerol mono-distearate | 0.7 |
| Cationic surfactant (for example lauryl trimethylammonium chloride) | 2.0 |
| Cholesterol | 0.2 |
| Soya lecithin | 0.3 |
| A mixture of cetylstearyl alcohol with nonionic emulsifiers ("Emulgade" A - *) | 8.0 |
| Perfume oil | 0.3 |
| Compound B or F | 3.0 |
| Water, fully deionized | 85.5 |
| 4. Skin cream | |
| Self-emulsifying mixture of mono/diglycerides of higher saturated fatty acids with potassium stearate ("Cutina" KD 16 - *) | 16.0 |
| Cetylstearyl alcohol containing approx. 12 moles of ethylene oxide ("Eumulgin" B1 - *) | 1.0 |
| 2-octyldodecanol | 6.0 |
| Isopropyl myristate | 4.0 |
| Glycerol | 6.0 |
| Compound E or G | 4.0 |
| Water | 63.0 |

(* - trademark of Henkel KGaA, Fed. Rep. of Germany)

Although certain embodiments of the invention have been described in detail, it will be appreciated that other embodiments are contemplated along with modification of the disclosed features, as being within the scope of the invention, which is defined in the appended claims.

We claim:

1. A sebosuppressive cosmetic composition containing a solution, mixture, or dispersion, in a base comprising at least one of water, alcohol, or oil, of an antiseborrheically effective amount of a p-alkoxy or p-alkylbenzyloxy benzoic acid ester corresponding to the following formula

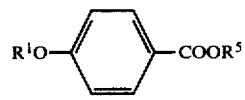

(I)

wherein $R^1$ is
(i) a branched alkyl group having from 6 to 18 carbon atoms,
(ii) an alkylbenzyl group wherein the alkyl moiety has from 3 to 9 carbon atoms, or
(iii) $R^2$—(O—Y)$_n$ wherein $R^2$ is an alkyl group having from 6 to 18 carbon atoms, or an alkylbenzyl group wherein the alkyl moiety has from 3 to 9 carbon atoms; Y is $CHR^3$—$CHR^4$; $R^3$ and $R^4$ independently represent a hydrogen or a methyl, and n = 1 or 2;

and $R^5$ is an alkyl group having from 1 to 4 carbon atoms, or a methoxy alkyl, an ethoxyalkyl, or a hydroxyalkyl having from 1 to 4 carbon atoms.

2. The sebosuppressive cosmetic composition of claim 1 wherein $R^1$ is a branched chain alkyl group having from 8 to 13 carbon atoms or alkylbenzyl group wherein the alkyl moiety has from 3 to 6 carbon atoms or $R^1$ is $R^2$—(O—Y)$_n$ where R is an alkyl group having from 9 to 14 carbon atoms and n = 1.

3. The sebosuppressive cosmetic composition of claim 2 wherein $R^1$ is a repeatedly branched alkyl group having from 8 to 13 carbon atoms.

4. The sebosuppressive cosmetic composition of claim 2 wherein the p-alkoxy or p-alkylbenzyloxy benzoic acid ester is selected from the group consisting of
- 4-(isononyloxy)-benzoic acid methylester,
- 4-(4-tert-butylbenzyloxy)-benzoic acid methylester,
- 4-(2-dodecyloxy-ethoxy)-benzoic acid methylester, and
- 4-(2-dodecyloxy-ethoxy)-benzoic acid-3-hydroxypropyl ester.

5. The sebosuppressive cosmetic composition of claim 1 wherein said antiseborrheically effective amount comprises between about 0.005 and 5.0 wt. %, of the total weight of said preparation.

6. The sebosuppressive cosmetic composition of claim 2 wherein said antiseborrheically effective amount comprises between about 0.005 and 5.0 wt. %, of the total weight of said preparation.

7. The sebosuppressive cosmetic composition of claim 5 wherein said antiseborrheically effective amount comprises between about 0.01 and 2.0 wt. %, of the total weight of said preparation.

8. The sebosuppressive cosmetic composition of claim 6 wherein said antiseborrheically effective amount comprises between about 0.01 and 2.0 wt. %, of the total weight of said preparation.

9. A method for reducing the production of sebum by the sebaceous cell in mammals which comprises topically contacting said sebaceous cell with an antiseborrheically effective amount of a p-alkoxy or a p-alkylbenzyloxy benzoic ester corresponding to the following formula

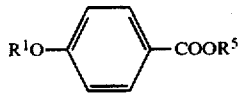

wherein $R^1$ is
(i) a branched alkyl group having from 6 to 18 carbon atoms,
(ii) an alkylbenzyl group wherein the alkyl moiety has from 3 to 9 carbon atoms, or
(iii) $R^2—(O—Y)_n$ wherein $R^2$ is an alkyl group having from 6 to 18 carbon atoms, or an alkylbenzyl group wherein the alkyl moiety has from 3 to 9 carbon atoms; Y is $CHR^3—CHR^4$; $R^3$ and $R^4$ independently represent a hydrogen or a methyl, and n=1 or 2;

and $R^5$ is an alkyl group having from 1 to 4 carbon atoms, or a methoxy alkyl, an ethoxyalkyl, or a hydroxyalkyl having from 1 to 4 carbon atoms.

10. The method of claim 9 wherein $R^1$ is a branched chain alkyl group having from 8 to 13 carbon atoms or alkylbenzyl group wherein the alkyl moiety has from 3 to 6 carbon atoms or $R^1$ is $R^2—(O—Y)_n$ where $R^2$ is an alkyl group having from 9 to 14 carbon atoms and n=1.

11. The method of claim 10 wherein $R^1$ is a repeatedly branched alkyl group having from 8 to 13 carbon atoms.

12. The method of claim 10 wherein the p-alkoxy or p-alkylbenzyloxy benzoic acid ester is selected from the group consisting of
- 4-(isononyloxy)-benzoic acid methylester,
- 4-(4-tert-butylbenzyloxy)-benzoic acid methylester,
- 4-(2-dodecyloxy-ethoxy)-benzoic acid methylester, and
- 4-(2-dodecyloxy-ethoxy)-benzoic acid-3-hydroxypropyl ester.

13. The method of claim 9 wherein said antiseborrheically effective amount comprises between about 0.005 and 5.0 wt. % of the total wt.

14. The method of claim 10 wherein said antiseborrheically effective amount comprises between about 0.005 and 5.0 wt. % of the total wt.

15. The method of claim 13 wherein said antiseborrheically effective amount comprises between about 0.01 and 2.0 wt. % of the total wt.

16. The method of claim 14 wherein said antiseborrheically effective amount comprises between about 0.01 and 2.0 wt. % of the total wt.

17. The sebosuppressive cosmetic composition of claim 1 consisting essentially of said antiseborrheic benzoic acid compound, and at least one of water, organic solvent, surfactant, oil, fat, wax, fragrance, dye, or preservative.

18. The sebosuppressive cosmetic composition of claim 17 comprising a hair lotion further containing water and an alcohol.

19. The sebosuppressive cosmetic composition of claim 17 comprising a shampoo for oily hair further containing a surfactant.

20. The sebosuppressive cosmetic composition of claim comprising a hair treatment preparation further containing an alcohol and a surfactant.

21. The sebosuppressive cosmetic composition of claim 17 comprising a skin cream further containing alcohol, glycerol, and glycerides.

* * * * *